United States Patent
Price et al.

(10) Patent No.: US 12,057,196 B1
(45) Date of Patent: Aug. 6, 2024

(54) ANISOTROPIC POOLING FOR CONTEXTUAL EMBEDDING OF A COMPOUND SEQUENCE

(71) Applicant: Amazon Technologies, Inc., Seattle, WA (US)

(72) Inventors: Layne Christopher Price, Seattle, WA (US); David Heckerman, Bellevue, WA (US)

(73) Assignee: Amazon Technologies, Inc., Seattle, WA (US)

( * ) Notice: Subject to any disclaimer, the term of this patent is extended or adjusted under 35 U.S.C. 154(b) by 502 days.

(21) Appl. No.: 17/209,486

(22) Filed: Mar. 23, 2021

(51) Int. Cl.
| | |
|---|---|
| G16B 30/10 | (2019.01) |
| G06N 3/08 | (2023.01) |
| G16B 40/00 | (2019.01) |
| G16B 50/30 | (2019.01) |

(52) U.S. Cl.
CPC ............ *G16B 30/10* (2019.02); *G06N 3/08* (2013.01); *G16B 40/00* (2019.02); *G16B 50/30* (2019.02)

(58) Field of Classification Search
None
See application file for complete search history.

(56) References Cited

PUBLICATIONS

Mirabello, Claudio, and Bjorn Wallner. "rawMSA: end-to-end deep learning using raw multiple sequence alignments." PloS one 14.8 (2019): e0220182. (Year: 2019).*

Li, Wenjuan, et al. "Anisotropic convolution for image classification." IEEE Transactions on Image Processing 29 (2020): 5584-5595. (Year: 2020).*

Zeng, Tao, Bian Wu, and Shuiwang Ji. "DeepEM3D: approaching human-level performance on 3D anisotropic EM image segmentation." Bioinformatics 33.16 (2017): 2555-2562. (Year: 2017).*

Bepler, Tristan, and Bonnie Berger. "Learning protein sequence embeddings using information from structure." arXiv preprint arXiv:1902.08661 (2019). (Year: 2019).*

Fukuda, Hiroyuki, and Kentaro Tomii. "DeepECA: an end-to-end learning framework for protein contact prediction from a multiple sequence alignment." BMC bioinformatics 21.1 (2020): 1-15. (Year: 2020).*

Yang, Kevin K., et al. "Learned protein embeddings for machine learning." Bioinformatics 34.15 (2018): 2642-2648. (Year: 2018).*

Altschul et al., "Basic Local Alignment Search Tool," J. Mol. Biol., 1990, vol. 215, pp. 403-410.

(Continued)

*Primary Examiner* — Larry D Riggs, II
*Assistant Examiner* — Mary C Leverett
(74) *Attorney, Agent, or Firm* — Kilpatrick Townsend & Stockton LLP

(57) ABSTRACT

Techniques are described and relate to anisotropic pooling for contextual embedding of a protein sequence. In an example, a system receives a first biological sequence and determines a sequence arrangement that comprises a component of the first biological sequence and a second biological sequence of components. By using an artificial intelligence (AI) model, the system determines a third sequence that comprises a contextual embedding vector corresponding to the component of the first biological sequence. The AI model generates the third sequence based at least in part on the sequence arrangement and by at least using a convolution and anisotropic pooling.

20 Claims, 10 Drawing Sheets

(56) References Cited

PUBLICATIONS

He et al., "Deep Residual Learning for Image Recognition," IEEE Conference on Computer Vision and Pattern Recognition (CVPR), 2016, pp. 770-778.
Rao et al., "MSA Transformer," BioRxiv, Available Online at: https://www.biorxiv.org/content/10.1101/2021.02.12.430858v1.full.pdf, Feb. 13, 2021, pp. 1-16.

* cited by examiner

Mangla et al.

ANISOTROPIC POOLING FOR CONTEXTUAL EMBEDDING OF A COMPOUND SEQUENCE

BACKGROUND

Analysis of nucleic acid or protein sequences can have various applications in the life sciences space. For instance, analysis of protein sequences supports the identification of a protein family to which the protein sequence belongs, the prediction of cellular localization of the protein, the prediction of the sequence of the gene encoding the protein, and the discovery of the structure and function of the protein, among other applications.

Artificial intelligence techniques are also used in the life sciences space. For instance, artificial intelligence models can be developed and deployed for diagnosis and disease identification, drug discovery, and vaccine development.

BRIEF DESCRIPTION OF THE DRAWINGS

Various embodiments in accordance with the present disclosure will be described with reference to the drawings, in which.

DETAILED DESCRIPTION

Figure 1:
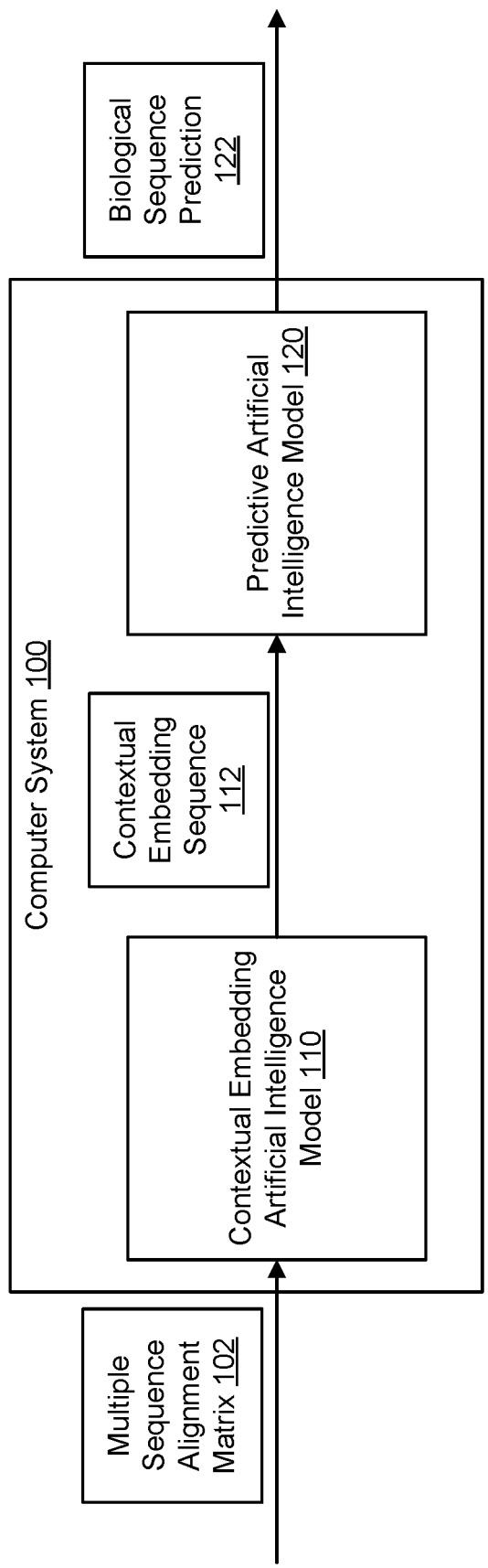
FIG. 1 illustrates an example of a computer system for protein sequence processing according to embodiments of the present disclosure.

In the following description, various embodiments will be described. For purposes of explanation, specific configurations and details are set forth in order to provide a thorough understanding of the embodiments. However, it will also be apparent to one skilled in the art that the embodiments may be practiced without the specific details. Furthermore, well-known features may be omitted or simplified in order not to obscure the embodiment being described.

Embodiments of the present disclosure relate to, among other things, anisotropic pooling for contextual embedding of a biological sequence. In an example, the biological sequence can be an amino acid or a nucleotide sequence. A biological sequence is received. An arrangement of biological sequences (e.g., a multiple sequence alignment (MSA) matrix) is generated and includes the biological sequence and related biological sequences. This arrangement has a length and a height, where the length corresponds to the total number of components in the biological sequence (and, as applicable, any padding), and where the height corresponds to the total number of biological sequences included in the arrangement. A contextual embedding sequence is generated by inputting the arrangement to an artificial intelligence (AI) model. The contextual embedding sequence includes an embedding vector for each component (e.g., amino acid or nucleotide) of the biological sequence, where the embedding vector is generated based on a context of the component within biological sequence, or subsequences thereof, and within the arrangement (e.g., based on information learned about the component given its position within the biological sequence and given the alignment and similarity of the biological sequence within the arrangement). To generate the contextual embedding sequence, the arrangement is represented as an image having the same length and height as the arrangement and an embedding dimension for each compound. The AI model iteratively performs convolution and anisotropic pooling on the image until the image's height is reduced to one, while preserving the length and updating the embedding. The resulting image has the same length as the arrangement, a height of one, and an embedding vector for each component of the biological sequence. In other words, the resulting image corresponds to the contextual embedding sequence. This contextual embedding sequence can be referred to as a consensus representation and can be used by one or more systems for biological sequence processing.

To illustrate, consider an example of a personalized vaccine for a person. A biopsy can be performed on tumor cells of the person. A target protein sequence is derived from the biopsy and compared (e.g., via an alignment algorithm) to a protein sequence of non-tumor cells of the person and to other known protein sequences (e.g., from Genbank or other sequence database) in order to identify variants related to the tumor. The personalized vaccine can be developed and can be targeted to the variants. The vaccine development can involve using an MSA matrix that includes the different protein sequences. Information from the MSA matrix can be input into a set of protein prediction AI models trained to predict, for example, protein secondary structure, cleavage sites, molecule binding, and/or T-cell recognition and response. In this example, the information can be a contextual embedding sequence that includes embedding vectors for each amino acid of the target protein sequence.

In particular, the target protein sequence has twenty amino acids. By using a sequence alignment algorithm (e.g., basic local alignment search tool (BLAST)), an MSA matrix is constructed and includes two-hundred protein sequences, each twenty amino acid long. The target protein sequence is included in a top row of the MSA matrix. Next, the MSA matrix is input into a contextual embedding AI model. A two-dimensional convolutional layer of the contextual embedding AI model generates an image based on the MSA matrix. The image has a length of twenty, a height of two hundred, and an initial embedding dimension of seventeen. In this way, each amino acid of the MSA matrix is represented with an embedding vector initially having seventeen elements. The image is input to an anisotropic max pooling layer of the contextual embedding AI model that reduces the height of the image by half, and preserves the length. Multiple encoding iterations are performed, where the output of the anisotropic max pooling layer is input to the two-dimensional convolutional layer and vice versa, and where the length is preserved, the height is reduced, and the embedding dimension is increased. During the last encoding iteration, the height is reduced to one and the resulting image is output as a consensus representation of the MSA matrix. This output has a length of twenty elements, a height of one, and an embedding dimension of fifty. In other words, each amino acid of the target protein sequence is represented by one embedding vector having fifty elements, where this embedding vector represents information learned about the amino acid given its context within the target protein sequence and the MSA matrix. The consensus representation is input to the set of protein prediction AI models.

Embodiments of the present disclosure provide various technological improvements. For example, a set of compound prediction AI models can include deep learning models for processing protein sequences and/or genome sequences. Many deep learning models necessitate the use of a sequence as the data structure of their input. However, better information can be learned from grouping evolutionary related sequences together in an arrangement, such as an MSA matrix. Embodiments of the present disclosure allow the conversion from this type of information (e.g., arrangement-based) into a sequence (e.g., contextual embedding sequence) without much loss to the usefulness and depth of the information. The converted information (e.g., contextual embedding sequence) can be input to the deep learning models that, in turn, can more robustly process protein sequences and genome sequences.

In the interest of clarity of explanation, various embodiments are described herein using examples of protein sequences and an MSA matrix. However, the embodiments are not limited to such examples, to merely protein sequences, or to merely MSA matrices. For example, the embodiments similarly apply to sequences of nucleotides and to genome sequencing. An MSA matrix is an example of a sequence arrangement, where the sequences are aligned based on local and/or global similarities between the compounds. Other sequence arrangements are possible, such as a grouping (e.g., a list) of sequences arranged according to one or more similarity criteria. Generally, the embodiments apply to generating a contextual embedding sequence for a biological sequence based on a sequence arrangement of multiple biological sequences. The biological sequence can include components, such as amino acids, nucleotides, or any other type of organic or synthetic compounds.

FIG. 1 illustrates an example of a computer system 100 for protein sequence processing according to embodiments of the present disclosure. The computer system 100 can host a contextual embedding AI model 110 and a predictive AI model 120. An arrangement of biological sequences, such as an MSA matrix 102, is input to the computer system 100. In one example, the biological sequences are protein sequences, although other types of biological sequences are possible. The contextual embedding AI model 110 generates and outputs a contextual embedding sequence 112 based on MSA matrix 102 to the predictive AI model 120. In turn, the predictive AI model 120 generates and outputs a biological sequence prediction 122, such as a prediction related to a target protein sequence.

In an example, the computer system 100 can be any suitable system that includes one or more processors and one or more memories storing computer-readable instructions executable by the one or more processors to configure the computer system 100 to host the two AI models 110 and 120, receive the MSA matrix 102, and output the biological sequence prediction 122. For instance, the computer system 100 may be a server or a cloud computing service hosted in a data center.

The MSA matrix 102 can be received from a user device or another computer system via a web interface or an application interface to the computer system 100. Additionally or alternatively, a target biological sequence (e.g., a target protein sequence) may be received by the computer system 100 that, in turn, generates the MSA matrix 102 from biological sequences (e.g., protein sequences) stored in data store local to the computer system 100 or remotely accessible to the computer system 100.

The computer system 100 can output the biological sequence prediction 122 to the user device, the other computer system, or any other system via the same web interface or application interface and/or another web interface or application interface. The biological sequence prediction 122 can be an output of processing performed by the predictive AI model 120.

This predictive AI model 120 (or a set of similar AI models) can be trained to perform different tasks, where the biological sequence prediction 122 can be one, a combination, or a collection of the tasks. Generally, the biological sequence prediction 122 includes a determination of a function and/or a structure of a biological sequence. In the present disclosure, rather than generating the biological sequence prediction 122 from the biological sequence itself, this prediction 122 is generated from the contextual embedding sequence 112.

In one example, the biological sequence prediction 122 can include a prediction of a protein structure, where the predictive AI model 120 includes multiple layers of multi-headed self-attenuation to predict the amino acid residue-specific location in Cartesian space for the $C_\alpha$ backbone. In another example, the biological sequence prediction 122 can include a prediction of binding to vaccine peptide candidates. In this example, major histocompatibility complex (MHC) alleles are represented in the contextual embedding sequence 112 or an MSA matrix is used for each allele. In both cases, the predictive AI model 120 is trained to output the binding prediction. In yet another example, vaccine candidates include peptides that match naturally occurring cancer peptides that are cleaved off from their parent protein. The region immediately surrounding a peptide in the parent protein is called the flanking region. Rather than best-guessing the flanking region for a given peptide, an MSA matrix of the parent proteins is used to derive a set of possible flanking regions. In this illustration, the biological sequence prediction 122 identifies the set of possible flanking regions with a high accuracy.

Each of the contextual embedding AI model 110 and the predictive AI model 120 can be implemented as an AI model trained specifically for a set of tasks. In the case of the contextual embedding AI model 110, the set of tasks includes outputting the contextual embedding sequence 112 based on the MSA matrix 102 (or any other grouping of information). In the case of the predictive AI model 120, the set of tasks includes outputting the biological sequence prediction 122 based on the contextual embedding sequence 112 (or any other sequence).

In an example, the contextual embedding AI model 110 is a first AI model that is implemented as a program code (e.g., a set of computer-readable instructions) stored in one or memories of the computer system 100 and executable by one or more processors of the computer system 100. Additionally or alternatively, this first AI model can be implemented on specialized hardware, such as a set of AI chips.

Similarly, the predictive AI model 120 is a second AI model that is implemented as a program code (e.g., a set of computer-readable instructions) stored in one or more memories of the computer system 100 and executable by one or more processors of the computer system 100. Additionally or alternatively, this second AI model can be implemented on specialized hardware, such as a set of AI chips. In different examples, the second AI model can include a set of deep learning models, such as long short-term memory (LSTM) machine learning (ML) models, transformers, and the like.

Although FIG. 1 illustrates that the computer system 100 includes the contextual embedding AI model 110 and the predictive AI model 120, embodiments of the present disclosure are not limited as such. For example, the predictive AI model 120 can be hosted on a different computer system. In this example, an application interface may include between the contextual embedding AI model 110 and the predictive AI model 120, or the two AI models 110 and 120 may have access to a same data store, where the contextual embedding AI model 110 can store the contextual embedding sequence 112 in the data store, and where the predictive AI model 120 can retrieve the contextual embedding sequence 112 from the data store.

Figure 2:
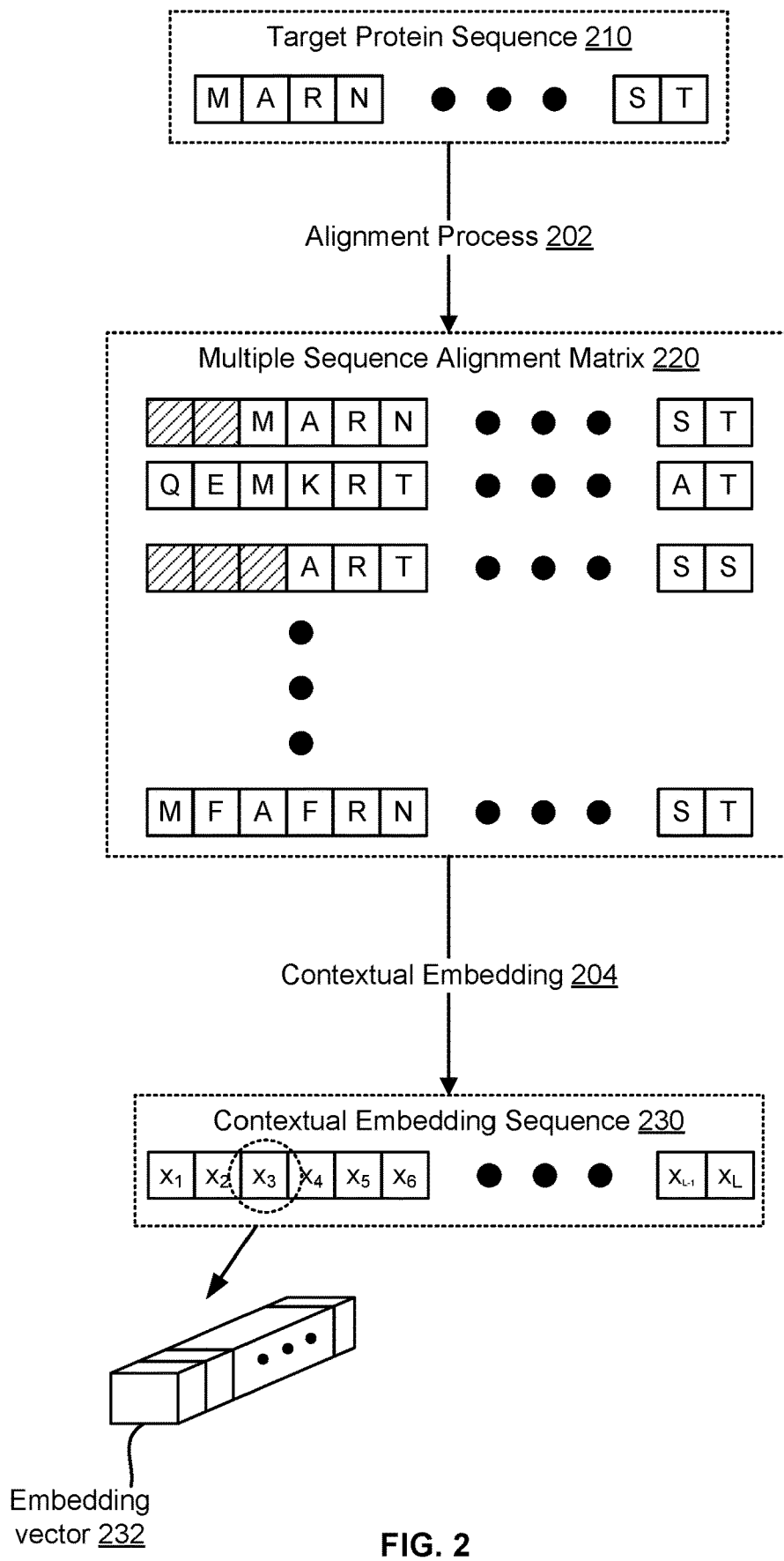
FIG. 2 illustrates an example of generating a multiple sequence alignment (MSA) matrix based on a target protein sequence and generating a contextual embedding sequence based on the MSA matrix according to embodiments of the present disclosure.

FIG. 2 illustrates an example of generating a multiple sequence alignment (MSA) matrix 220 based on a target protein sequence 210 and generating a contextual embedding sequence 230 based on the MSA matrix 220 according to embodiments of the present disclosure. In particular, a computer system (e.g., the computer system 100) can receive the target protein sequence 210, perform a look-up to a data store storing protein sequences to determine related protein sequences, and generate the MSA matrix 220 that includes the target protein sequence 210 and the related protein sequences. The same computer system or a different computer system (e.g., the computer system 100) can also input the MSA matrix 220 to a contextual embedding AI model (e.g., the contextual embedding AI model 110) to generate the contextual embedding sequence 230.

In an example, the target protein sequence 210 can be generated from a biopsy of tumor cells, e.g., by mass spectrometry or Edman degradation, or being derived from a nucleic acid sequence (e.g., RNA or genomic DNA) from the cells, and can have a certain length. This length corresponds to the total number of amino acids that are included in the protein sequence 210, such as in the range of ten to five-hundred.

The MSA matrix 220 represents a structure that groups the target protein sequence 210 with related protein sequences. An alignment process 202 can be applied to the different protein sequences based on the sequences of amino acids included therein. For instance, the protein sequences are aligned to identify regions of similarity that may be a consequence of functional, structural, or evolutionary relationships between the protein sequences. The aligned sequences of amino acids are represented as rows within a matrix. Gaps may be inserted between the amino acids so that identical or similar characters (each character representing an amino acid) are aligned in successive columns. Different alignment techniques are possible including computational approaches for global alignments and/or local alignments. Calculating a global alignment is a form of global optimization that spans the entire length of all query sequences. A local alignment identifies regions of similarity within long sequences that are often widely divergent overall. A variety of computational algorithms are available, such as a BLAST process or a Clustal Omega program.

In the illustration of FIG. 2, the MSA matrix 220 is organized in columns and rows. The first row includes the target protein sequence 210. The remaining rows include the aligned protein sequences. The number of columns define the length "L" of the MSA matrix 220 and this length "L" can be in the range of ten to fifty, for instance. The number of rows define a height "H" of the MSA matrix 220 and this height "H" can be in the range of ten to five-hundred, for instance. The intersection of a row and a column corresponds to an amino acid of that protein sequence. If a particular sequence is shorter than the length "L", padding can be added (shown in FIG. 2 with diagonally dashed rectangles). Further, based on the alignment, gaps (not shown in FIG. 2) can be also inserted. Padding and gaps can be represented programmatically with the same or different values, such as zeros and ones.

Prior to being input into the contextual embedding AI model, various processing can be applied to the MSA matrix 220. In one example, the rows are randomly shuffled. The shuffling may not include the top row (e.g., the target protein sequence 210). In another example, if a target height of the MSA matrix 220 is desired and if the number of aligned protein sequences is larger than the target height, one or more of the protein sequences can be randomly selected and removed, thereby truncating the MSA matrix 220. Here also, the truncating may exclude the top row. Conversely, if the number of aligned protein sequences is smaller than the target height, one or more of the protein sequences can be randomly selected and added to random rows of the MSA matrix 220, thereby increasing its height to meet the target. Here also, augmenting the MSA matrix 220 may exclude the top row.

Contextual embedding 204 is performed on the MSA matrix 220 to generate the contextual embedding sequence 230. This contextual embedding 204 includes inputting the MSA matrix to the contextual embedding AI model. The contextual embedding sequence 230 has the same length "L", a smaller height (typically one, as shown in FIG. 2), and an embedding dimension "D." The length "L" corresponds to the number of embedding vectors "$x_i$" that are included in the contextual embedding sequence 230. Each embedding vector "$x_i$" (where $1 \le i \le L$) corresponds to one of the amino acids of the target protein sequence 210 or, as applicable, one of the padding or gaps added thereto. Further, each embedding vector "$x_i$" has the embedding dimension "D" (e.g., its total number of elements is equal to "D"), where "D" can be in the range of ten to two hundred, for instance. In this way, each embedding vector corresponding to an amino acid embeds information about the amino acid given the context of the amino acid in the target protein sequence 210 and in the MSA matrix 220. In other words, the embedding vector represents vocabulary embedding based on learning an embedding for the amino acid in the vocabulary. Each vocabulary element "$y_i$" (e.g., each amino acid) is assigned a fixed dimensional vector "$x_i \in \mathbb{R}^D$," where "D" is the dimension of the embedding.

For example, FIG. 2 illustrates an embedding vector 232 (shown as being "$x_3$") corresponding to the first amino acid "M" in the target protein sequence 210. This embedding vector has "D" elements, each including a mathematical representation of information learned about the first amino acid "M" given its first position in the target protein sequence 210, other amino acids in this sequence 210, and other amino acids aligned in the remaining protein sequences of the MSA matrix 220.

Figure 3:
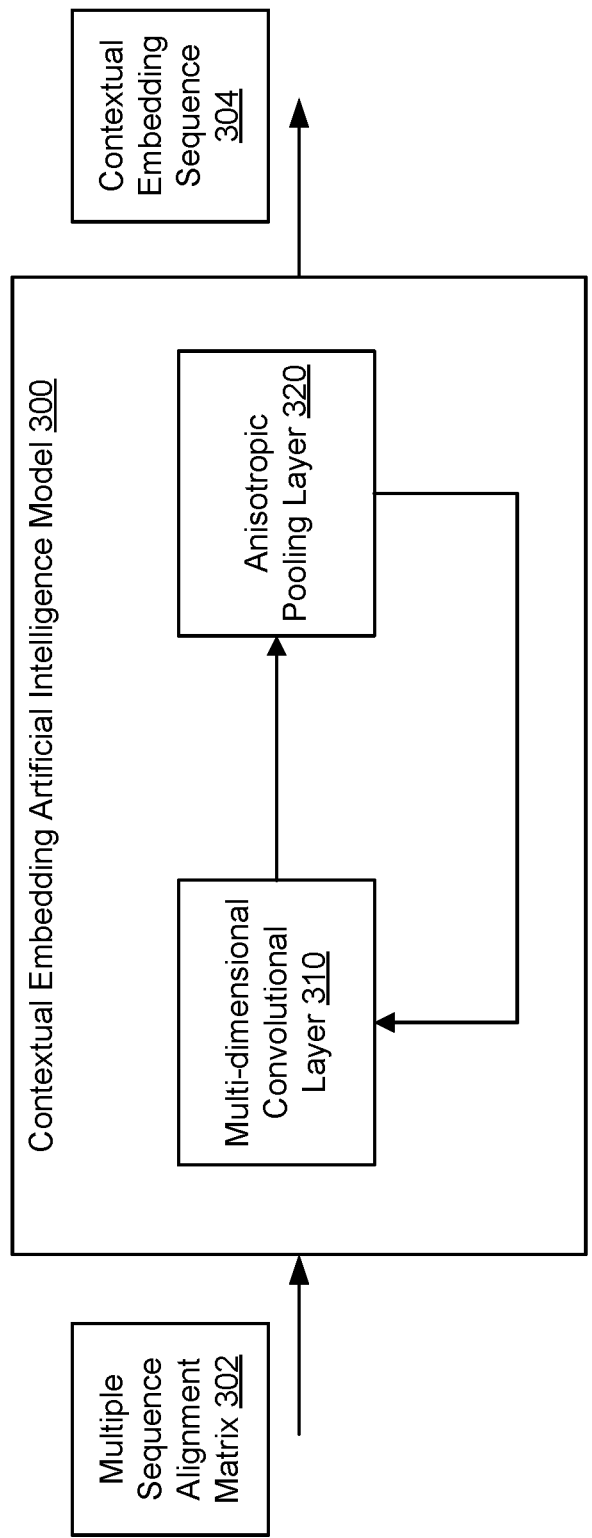
FIG. 3 illustrates an example of an artificial intelligence (AI) model that generates a contextual embedding sequence based on a MSA matrix according to embodiments of the present disclosure.

FIG. 3 illustrates an example of a contextual embedding AI model 300 that generates a contextual embedding sequence 304 based on a MSA matrix 302 according to embodiments of the present disclosure. In an example, the contextual embedding AI model 300 is implemented as an encoder that encodes the contextual embedding sequence 304 (e.g., the contextual embedding sequence 230 of FIG. 2) in response to receiving the MSA matrix 302 (e.g., the MSA matrix 220 of FIG. 2) as input. In the encoder implementation, the contextual embedding AI model 300 includes a multi-dimensional convolutional layer 310 and an anisotropic pooling layer 320 (e.g., with an iterative encoding loop between the two layers 310 and 320).

In an example, inputting the MSA matrix 302 includes generating an image representation of the MSA matrix 302, where the image representation is input to the multi-dimensional convolutional layer 310. For instance, each amino acid in the MSA matrix 302 is substituted with a D-dimensional embedding vector "$x_i$", resulting in an image having a length "L", a height "H", and an embedding dimension "$D_{in}$" (e.g., a tensor of dimension ($D_{in}$; H; L), where "H" is the number of sequences in the MSA matrix 302 and "L" is the length of the longest sequence in the MSA matrix 302. Each dimension of "$x_i$" can be interpreted as an image channel, effectively representing the MSA matrix 302 as a multi-channel image.

In the initial encoding iteration, the multi-channel image is input to the multi-dimensional convolutional layer 310. The multi-dimensional convolutional layer 310 applies a multi-dimensional convolution (e.g., a two-dimensional convolution) to further embed and update the embedding vectors "$x_i$". The embedding dimension "$D_{in}$" is updated (e.g., increased) to an embedding dimension "$D_{out}$". The length "L" and the height "H" are preserved. The output of the dimensional convolutional layer 310 is an updated multi-channel image (where the number of channels equals "$D_{out}$") that is input to the anisotropic pooling layer 320. In the next encoding iteration, the output of the anisotropic pooling layer 320, which is another updated multi-channel image (with a reduced height "H" as further described herein below) is input to the multi-dimensional convolutional layer 310. Multiple encoding iterations may be repeated until the height of the multi-channel image is reduced to a particular target height (e.g., one) and/or the embedding dimension "$D_{out}$" is increased to a target embedding dimension.

In an example, the multi-dimensional convolutional layer 310 learns local features in the input multi-channel image by two-dimensional convolutions. The combination of kernel size, padding, and stride of the multi-dimensional convolutional layer 310 are chosen such that the height "H" and the length "L" are not altered in the convolution. Different types of two-dimensional convolutions are possible including, for instance, nonlinearity function or a ResNet architecture. Below is an example implementation of the multi-dimensional convolutional layer 310, with a kernel size of three, a padding of one, and a stride of one (N referenced below is the batch size):

x=get image( )
x has dimensions N×D×H×L
conv=torch.nn.Conv2d(in_channels=D,
    out_channels=D_out,
    kernel_size: 3, stride=1, padding=1)
y=conv(x)
y has dimensions N×D_out×H×L.

The anisotropic pooling layer 320 performs anisotropic pooling on each channel of the multi-channel image received from the multi-dimensional convolutional layer 310. The anisotropic pooling may, but need not, use the same configurations (e.g., operator, kernel size, padding, stride) across the different channels. In an example, the operator is max pooling, although other operators are possible, such as average pooling.

The kernel is anisotropic such that the kernel size allows the reduction of the height of the multi-channel image while preserving its length across the encoding iterations. For instance, the kernel has a height and a length that are different from each other. For image height reduction and image length preservation, the height of the kernel can be larger than the length.

In an example, the kernel size is variable, where its value is based on the encoding iteration and/or the total number of sequences included in the MSA matrix 302 (e.g., the height of the initial multi-channel image). The purpose of using a variable kernel size is to, for instance, support the ability to reduce the height of the multi-channel image to a target height (e.g., one). The variability can be across the height of the kernel, whereby its length is kept the same (to avoid changes to the length of the multi-channel image). For instance, the length of the kernel size is constant and is equal to one. A kernel size of value "h" indicates a height of "h" and a length of "1". As such, a kernel size of "2" indicates that the height of the kernel is two and its length is one. The larger number of encoding iteration, the smaller the kernel size can be made. Further, the kernel sizes are chosen such that the height of the multi-channel image can be divisible and reduced to the target height (e.g., one). As such, with the target height of one, the kernel size varies with the number of decoding iterations such that the product of these sizes is equal to the original height of the height of the multi-channel image.

To illustrate, consider the example of using five encoding iterations to reduce the height of the multi-channel image from two hundred to one. In this case, the kernel size is selected from a set of kernel sizes: {2, 2, 2, 5, 5}. The product of the elements of this set is equal to the height of the multi-channel image (two hundred), indicating that this height can be reduced to one upon completion of the encoding iterations. In the first encoding iteration, the kernel size of "2" is used (the first element in the set), thereby reducing the height to one-hundred. In the second encoding iteration, the kernel size of "2" is used (the second element in the set), thereby reducing the height to fifty. In the third encoding iteration, the kernel size of "2" is used (the third element in the set), thereby reducing the height twenty-five. In the fourth encoding iteration, the kernel size of "5" is used (the fourth element in the set), thereby reducing the height to five. In the fifth and last encoding iteration, the kernel size of "5" is used (the fifth element in the set), thereby reducing the height to the target height of one.

In an example, the stride is equal to the kernel size (e.g., to the kernel height). The padding can be set to zero when, for instance, the kernel length is one because the length of the multi-channel image is preserved.

Below is an example implementation of the anisotropic pooling layer 320, with an anisotropic kernel size of two:

aniso_kernel=(2,1)
aniso_max_pool=torch.nn.MaxPool2d
   (kernel_size=aniso_kernel, stride=aniso_kernel, padding=0)
y has dimensions N×D_out×H×L z=aniso_max_pool(y)
z has dimensions N×D_out×H/2×LL.

In the above example, the max pooling operator is used with kernel size, stride, and padding determined such that the height of the multi-channel image is reduced by a specific factor $\lambda \in \mathbb{N}$. If $\lambda=2$, the image height is reduced in half at the end of each encoding iteration.

The iterative encoding loop is used a number of times, until the final output has dimension (N, $D_f$, $H_T$, L), where $D_f$ is the final embedding dimension and "$H_T$" is the target height (e.g., "$H_T=1$"). When the target height is equal to one, the height dimension can be dropped, resulting in the contextual embedding sequence 304 having a length "L" (the same length as the MSA matrix 302) an embedding dimension of "D".

Figure 4:
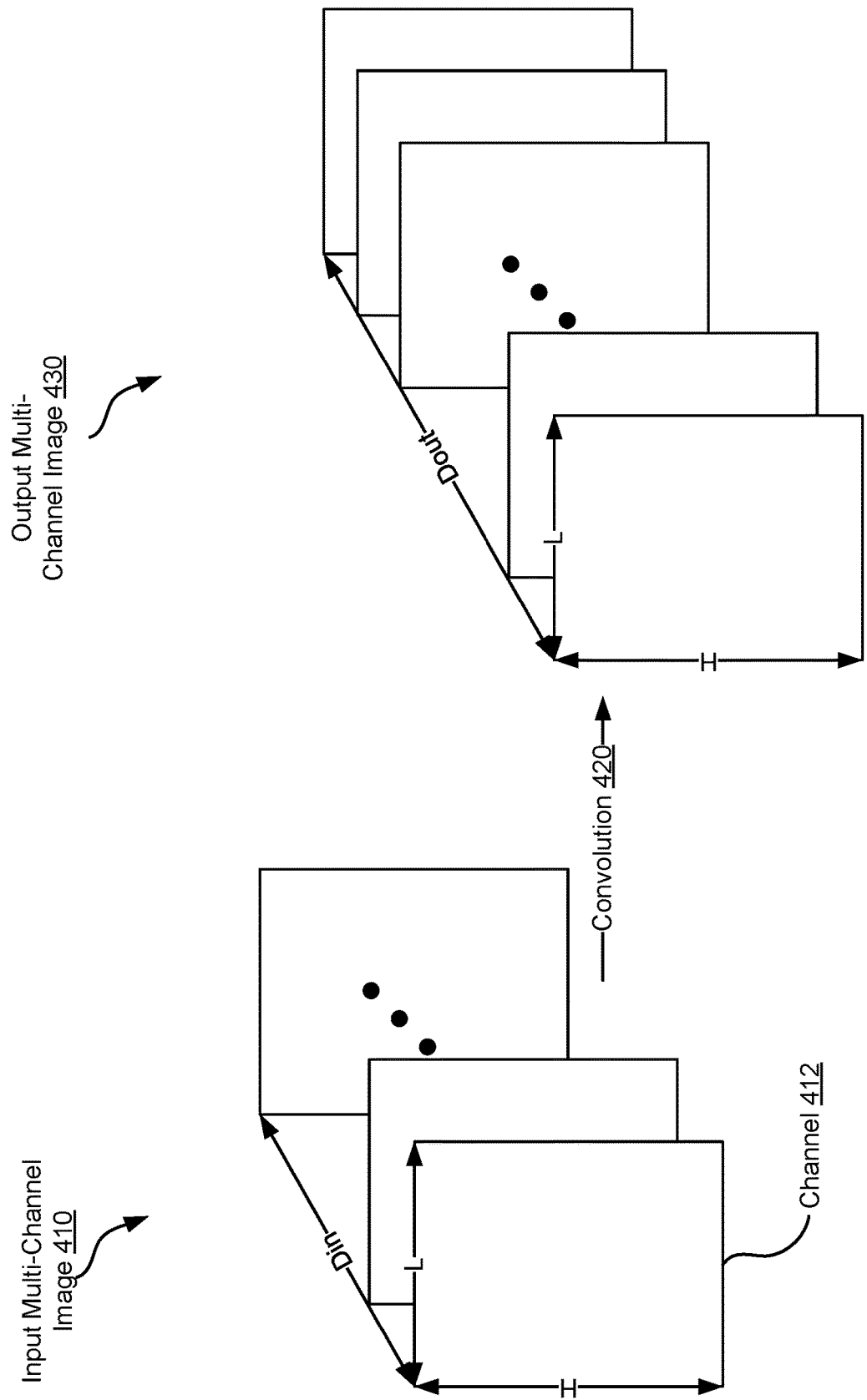
FIG. 4 illustrates an example of input and output of a convolutional layer of an AI model according to embodiments of the present disclosure.

FIG. 4 illustrates an example of input and output of a convolutional layer of an AI model according to embodiments of the present disclosure. In an example, the convolutional layer corresponds to the multi-dimensional convolutional layer 310 of FIG. 3. As illustrated, the input is an input multi-channel image 410 and the output is an output multi-channel image 430 generated after a convolution 420 (e.g., a two-dimensional convolution) during an encoding iteration.

The input multi-channel image 410 has a length "L", a height "H", and an embedding dimension "$D_{in}$". The length corresponds to the length of the represented MSA matrix. The height "H" is function of the encoding iteration. In the first encoding iteration, the height "H" is equal to the height of the represented MSA matrix. In subsequent encoding iterations, the height "H" is increasingly reduced by a factor $\lambda \in \mathbb{N}$ (e.g., from a set of {2, 3, 4, 5, . . . }). The dimension "$D_{in}$" can also be a function of the encoding iteration, whereby "$D_{in}$" increases with the increase to the number of the encoding iteration.

As explained herein above, an amino acid is represented by an embedding vector "$x_i$" having an embedding dimension that can be equal to "$D_{in}$". Initially, each amino acid from the MSA matrix is represented by embedding vector "$x_i$". Each channel 412 includes the pixels (e.g., elements) from the embedding vectors at the corresponding element location. For instance, channel "1" includes the first elements from the embedding vectors and represents a two-dimensional image having "L" by "H" pixels, each pixel being one of the first elements. In comparison, channel "j" includes the "jth" elements from the embedding vectors and represents another two-dimensional image having "L" by "H" pixels, each pixel being one of the "jth" elements. After the first encoding iteration and subsequent encoding iteration, the height "H" is reduced and each pixel in each channel no longer corresponds to one amino acid and, instead, represents learned information about a collection of amino acids.

The output multi-channel image 430 has also the same length "L" and height "H." However, its embedding dimension "$D_{out}$" can be different from "$D_{in}$" (e.g., can be larger). The value of each pixel per channel or, equivalently, the values of each embedding vector "$x_i$" across the channels are updated by the convolution 420.

Figure 5:
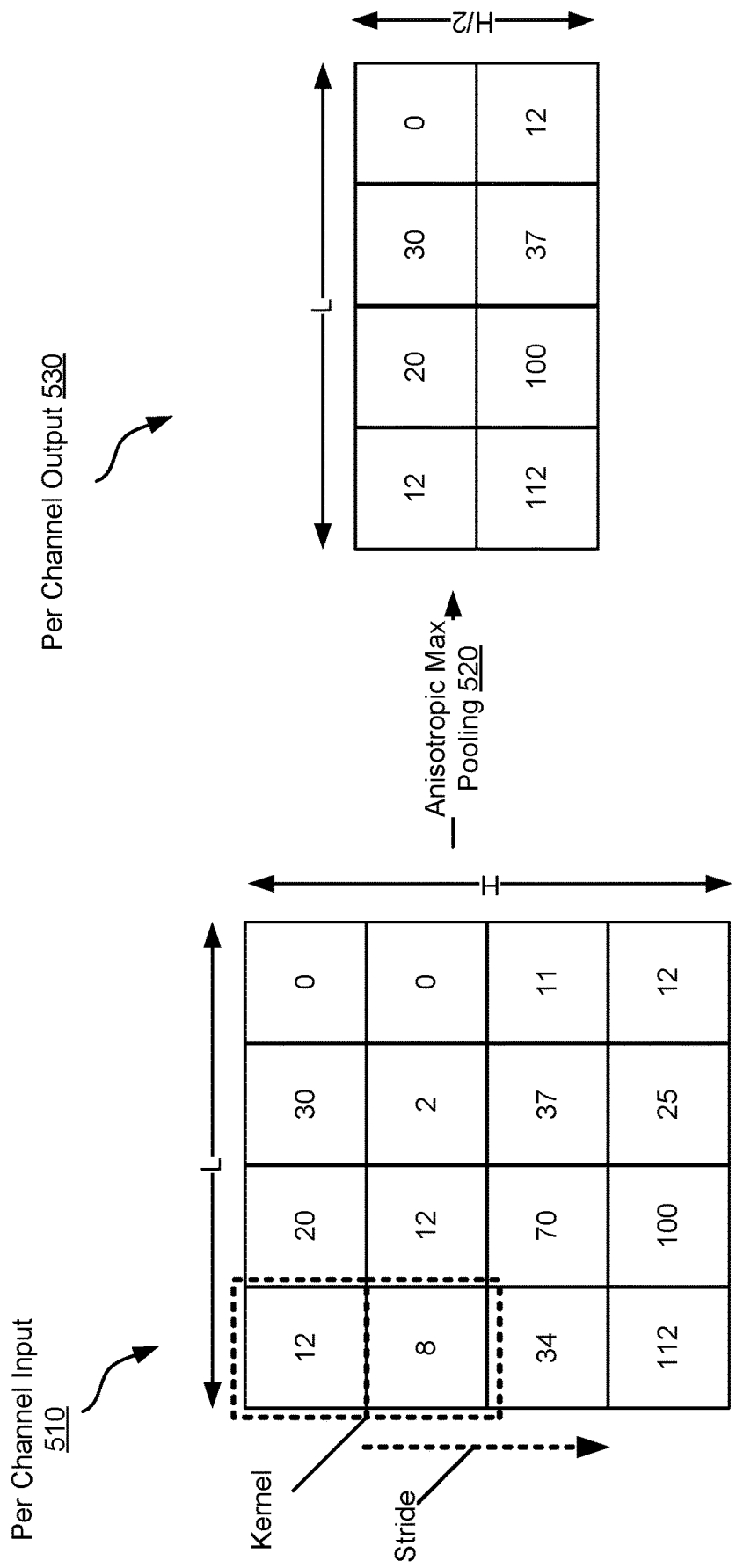
FIG. 5 illustrates an example of input and output of an anisotropic pooling layer of an AI model according to embodiments of the present disclosure.

FIG. 5 illustrates an example of input and output of an anisotropic pooling layer of an AI model according to embodiments of the present disclosure. In an example, the convolutional layer corresponds to the anisotropic pooling layer 320 of FIG. 3. As illustrated, anisotropic max pooling 520 with a kernel size of (2, 1) a stride of (2, 1), and a padding of zero is used per channel. Hence, if a multi-channel image is received, the anisotropic max pooling 520 is performed sequentially or in parallel across the channels. A per channel input 510 is received and a per channel output 530 is generated, where the "per channel" terminology is used to indicate that the anisotropic max pooling 520 is performed on a per channel basis. The per channel input 510 can include an arrangement of elements (e.g., pixels of a two-dimensional image) having a length "L" (the same length as the input MSA matrix) and a height "H". The anisotropic max pooling 520 reduced height "H" by a factor $\lambda$ (shown in FIG. 2 as "$\lambda=2$") while preserving the length "L". As a result, the per channel output 530 has the same length "L" and a reduced height (in the illustrated example of FIG. 2, a height of "H/2").

At the start of the anisotropic max pooling 520, the kernel can be positioned at a particular location in the top of two of the input 510 (e.g., the top, left corner). Given its (2, 1) size, the kernel represents a filter or mask that selects the maximum value between the two pixels covered by the filter or mask. Accordingly, when positioned in the top, left corner (as shown with the dotted rectangle in FIG. 5), the two masked pixels having values of "12" and "8" and the anisotropic max pooling 520 selects the value of "12" and removes the other value. The kernel moves to the next column by one given the (2, 1) stride, and the anisotropic max pooling 520 is performed again. This horizontal movement is repeated until the kernel reaches the last column (e.g., the one on the right), resulting in the top row of the output 530. Thereafter, the kernel is moved by two rows down give the (2, 1) stride and the anisotropic max pooling 520 is repeated horizontally until the last column is reached, resulting in the bottom row of the output 530.

Other kernel sizes and strides can be used. Further, other operators (e.g., average pooling) are possible. Also, other processing sequences are possible, such as starting from the bottom-left, top-right, or bottom-right, or such as vertical processing followed by horizontal processing.

Figure 6:
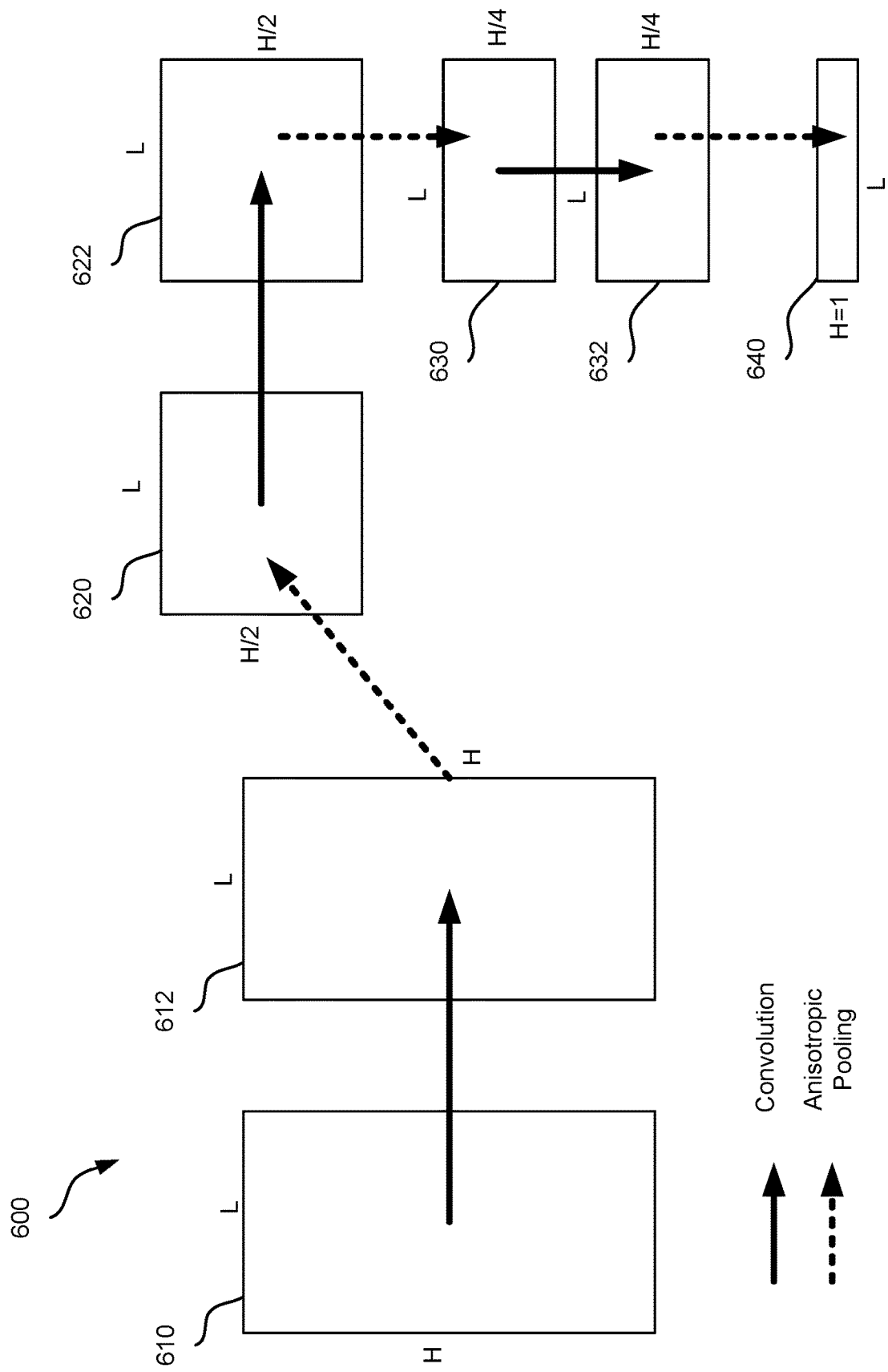
FIG. 6 illustrates an example of convolution and anisotropic pooling operations for generating a contextual embedding sequence based on a MSA matrix according to embodiments of the present disclosure.

FIG. 6 illustrates an example of convolution and anisotropic pooling operations 600 for generating a contextual embedding sequence based on an MSA matrix according to embodiments of the present disclosure. In the interest of clarity of explanation, convolution operations are described as being performed on a channel. However, as described herein above, the convolution operations can be performed on multiple channels. The batch dimension and channel dimension are omitted for clarity.

The left rectangle represents an image 610 of an MSA matrix. The bottom right rectangle represents a contextual embedding sequence 640 generated by the convolution and anisotropic pooling operations 600 upon processing the image. A solid arrow represents a two-dimensional convolution that preserves the length and height of an input. A dotted arrow represents an anisotropic pooling performed an output of a convolution, where the anisotropic pooling preserves the length and collapses the height of the input.

For illustrative purposes, consider the length "L" and the height "H" of the initial image 610 (the left rectangle) to be six and eight. Three encoding iterations are used with anisotropic max pooling having a kernel size of (2,1) to collapse this initial image 610 into a consensus sequence 640 having a height of one.

Accordingly, in the first encoding iteration, a convolution is performed on the initial image 610 resulting in an embedding image 612 having the same length "L" of six and the same height "H" of eight. Also in this first encoding iteration, an anisotropic max pooling is applied to the embedding image 612 resulting in an embedding image 620 having a the same length "L" of six and a reduced height "H" of four. This embedding image 620 is used as an input in the next encoding iteration. In this second encoding iteration, a convolution is performed on the embedding image 620 resulting in another embedding image 622 of the same length "L" of six and the same height "H" of four, followed by an anisotropic max pooling on the embedding image 622 resulting in an embedding image 630 having the same length "L" of six and a reduced height "H" of two. In the third and last encoding iteration, a convolution is performed on the embedding image 630 resulting in another embedding image 632 of the same length "L" of six and the same height "H" of two, followed by an anisotropic max pooling on the embedding image 632 resulting in the contextual embedding sequence 640.

Figure 7:
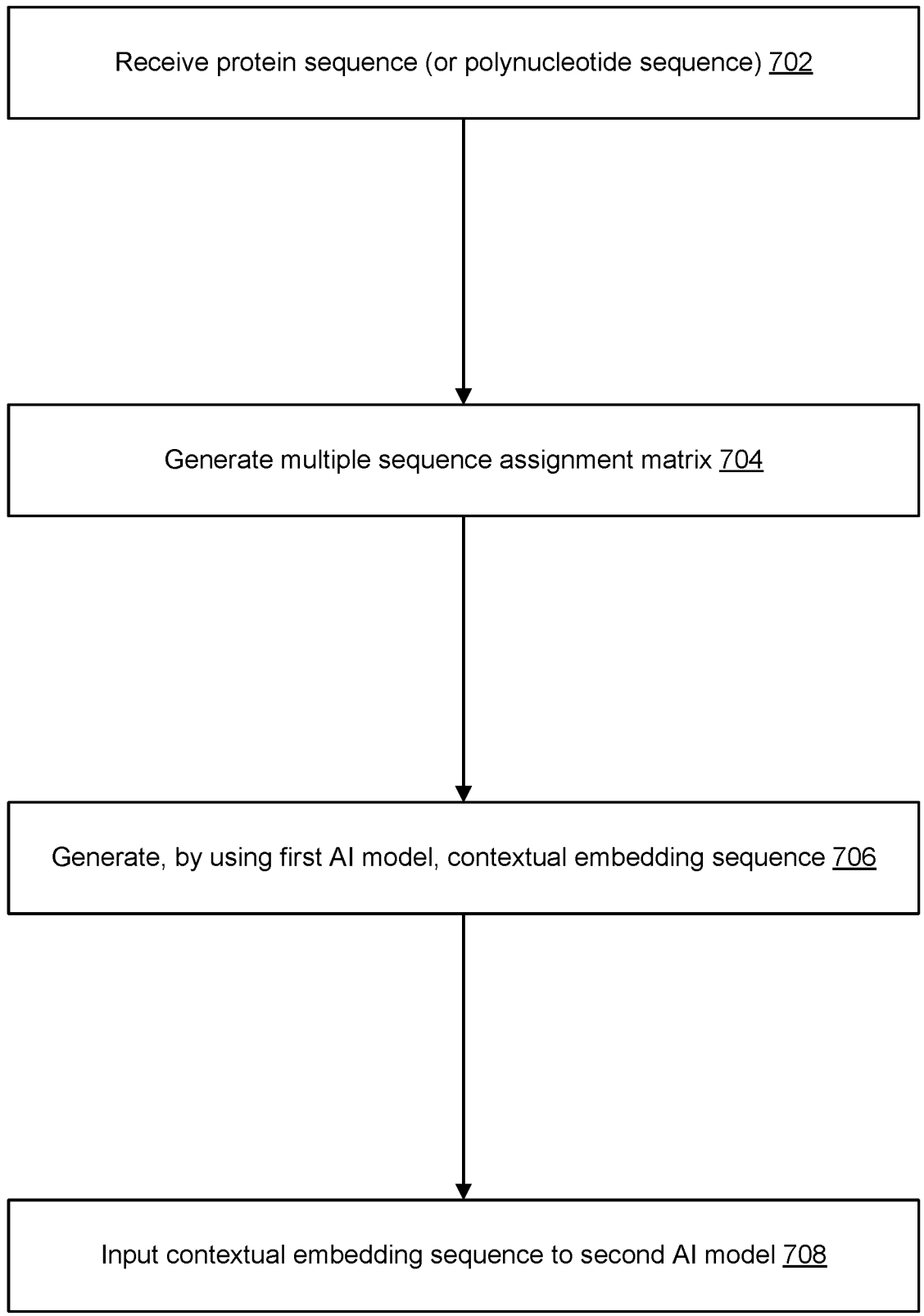
FIG. 7 illustrates an example of a flow for generating a contextual embedding sequence based on a MSA matrix according to embodiments of the present disclosure.

FIG. 7 illustrates an example of a flow for generating a contextual embedding sequence based on an MSA matrix according to embodiments of the present disclosure. A computer system, similar to the computer system of FIG. 1, is described as performing operations of the example flow of FIG. 7. Instructions for performing the operations can be stored as computer-readable instructions on one or more non-transitory computer-readable media of the computer system. As stored, the instructions represent programmable modules that include code or data executable by one or more processors of the computer system. The execution of such instructions configures the computer system to perform the specific operations shown in the corresponding figure and described herein. Each programmable module in combination with the respective processor(s) represents a means for performing a respective operation(s). While the operations are illustrated in a particular order, it should be understood that no particular order is necessary and that one or more operations may be omitted, skipped, and/or reordered. Further, and as described herein above, a sequence of amino sequence is described. However, the flow similarly applies to a sequence of nucleotides or other compounds.

In an example, the flow can start operation 702, where the computer system receives a protein sequence (and/or, similarly, a polynucleotide sequence or any other biological sequence). For instance, this protein sequence is a first sequence that includes amino acids and for which a protein prediction (or biological sequence prediction) is desired. Referring back to FIG. 2, the protein sequence can be the target protein sequence 210 and can be received from a user device or another computer system upon biopsy and mass spectrometry of tumor cells.

At operation 704, the computer system generates an MSA matrix based on the protein sequence (or any other arrangement of biological sequences). For instance, a BLAST process or another alignment tool is used, whereby the computer system uses the protein sequence in a query of a data store storing a plurality of protein sequences, and whereby the query engine returns a query result that includes an MSA matrix that includes an alignment of related protein sequences. Referring back to FIG. 2, the query result includes the MSA matrix 220. Other arrangements of the related protein sequences is possible and needs to be limited to a matrix.

At operation 706, the computer system generates, by using a first AI model, a contextual embedding sequence. For example, the first AI model includes the contextual embedding AI model 110 of FIG. 1 or the contextual embedding AI model 300 of FIG. 3. The MSA matrix (or the arrangement of protein sequences determined at operation 704) are input to the first AI model. This AI model uses a convolution and an anisotropic pooling to output the contextual embedding sequence. The convolution and the anisotropic pooling can be iteratively repeated. The MSA matrix can be represented with a multi-channel image that is input to a multi-dimensional convolutional layer of the first AI model. At each encoding iteration, the height and length of the multi-channel image are preserved, whereas its embedding dimension can be changed (e.g., increased). The output of the multi-dimensional convolutional layer is input into an anisotropic pooling layer of the first AI model. At each encoding iteration, the height and the embedding dimension are preserved, whereas the height can be reduced. The output of the anisotropic pooling layer is input to the multi-dimensional convolutional layer and multiple encoding iterations can be repeated until the height is reduced to a target height (e.g., one). The kernel size, stride, and/or padding of the anisotropic pooling layer can vary with the encoding iterations such that the length and embedding dimension are preserved and the height is reduced to the target height. The output of the anisotropic pooling layer at the last iteration corresponds the contextual embedding sequence.

At operation 708, the computer system inputs the contextual embedding sequence to a second AI model. For example, the second AI model includes the predictive AI model 120 of FIG. 1. The second AI model uses the contextual embedding sequence to generate and output a protein prediction (or any other biological sequence prediction), similar to the biological sequence prediction 122 of FIG. 1.

Figure 8:
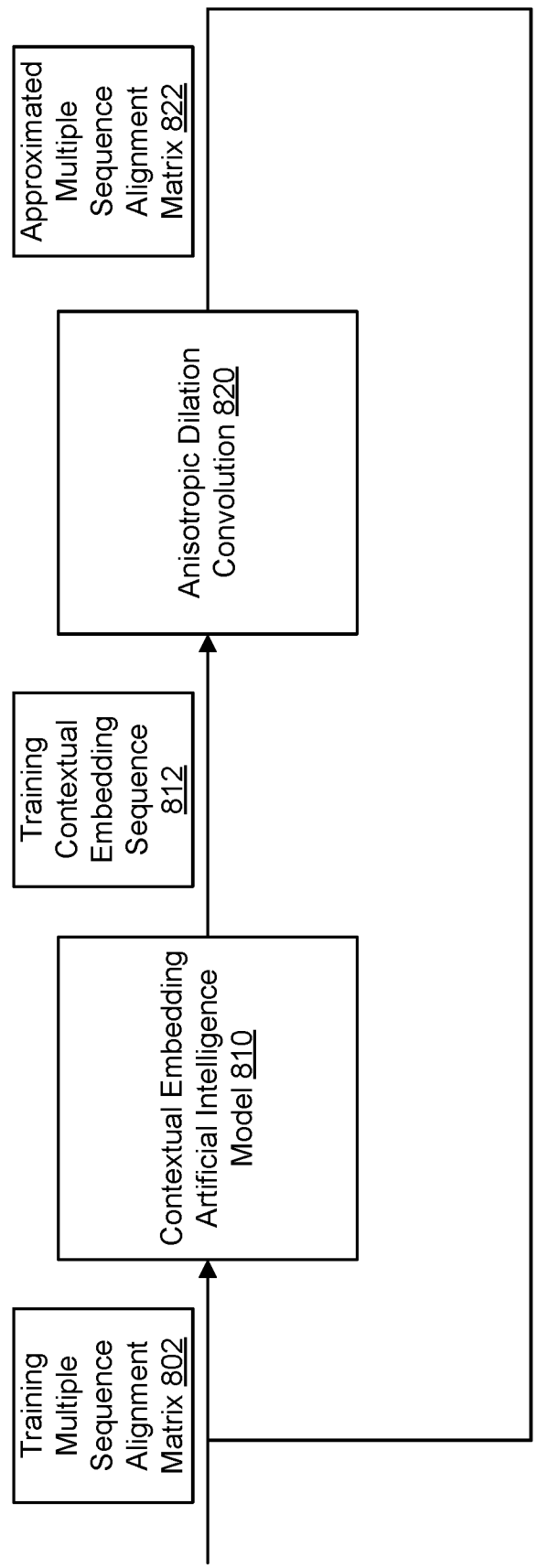
FIG. 8 illustrates an example of training an AI model to generate a contextual embedding sequence based on a MSA matrix according to embodiments of the present disclosure.

FIG. 8 illustrates an example of training an AI model to generate a contextual embedding sequence based on an MSA matrix according to embodiments of the present disclosure. In an example, the training is unsupervised training, although other types of training are possible. In an example, multiple protein sequences are available (e.g., from a data store). An MSA matrix is generated for each (e.g., the protein sequence is included in the top row of this matrix and other related protein sequences are found and aligned therewith) and represents a training MSA matrix. The anisotropic alignment reduction architecture is used to convert each training MSA matrix into a training contextual embedding sequence (e.g., a corresponding consensus representation). Thereafter, the inverse of this architecture, where the inverse operation to the anisotropic pooling is an anisotropic dilated convolution, to reconstructing the original training MSA matrix for each of the training contextual embedding sequences. Each reconstructed training MSA matrix is compared to the corresponding original training MSA matrix. This process can be repeated across the various training MSA matrices to update parameters of the AI model (e.g., weights of the connections of the nodes in the convolutional layer by using backpropagation).

In the illustration of FIG. 8, a first protein sequence is used and a corresponding training MSA matrix 802 is generated. This training MSA matrix 802 is input to a contextual embedding AI model 810 that includes a multi-dimensional convolutional layer and an anisotropic pooling layer. The contextual embedding AI model 810 outputs a training contextual embedding sequence 812. An anisotropic dilation convolution 820 is performed on the training embedding sequence 812 to dilate the training embedding sequence 812 in order to have the same size (e.g., length and height) as the training MSA matrix 802 and approximate, through convolution, the training MSA matrix 802. The output of the anisotropic dilation convolution 820 is an approximated MSA matrix 822. The training MSA matrix 802 and this approximated training MSA matrix 822 are compared to compute an error. Different techniques to compute the errors are possible, such as the difference between the two matrices 802 and 822. Backpropagation is used to update the parameters of the multi-dimensional convolutional layer of the contextual embedding AI model 810 in order to reduce the error. This process can be iterative across many training MSA matrices.

The above-unsupervised training approach allows training the contextual embedding AI model 810 without the need to have labels. However, if training data is labeled and available, a supervised training approach can be additionally or alternatively used. For example, and referring back to FIG. 1, two AI models can be trained together. The first AI model is a contextual embedding AI model, and the second AI model is a predictive AI model. The first AI model is trained to generate contextual embedding sequences. The second AI model is trained to output protein predictions (or, similarly, biological sequence predictions). In this example, the training data includes training MSA matrices, each labeled with a corresponding protein prediction (or, similarly, biological sequence prediction). The labels are used as ground truth during the training. Accordingly, an MSA training matrix having a label is input to the first AI model that generates a corresponding training contextual embedding sequence. This sequence is input to the second AI model that generates a corresponding protein prediction (or biological sequence prediction). The protein prediction or biological sequence prediction is compared to the label to adjust a cost function. Backpropagation is used to update the parameters of the two AI models to reduce or minimize the cost function. This process can also be iterative across many training MSA matrices.

Figure 9:
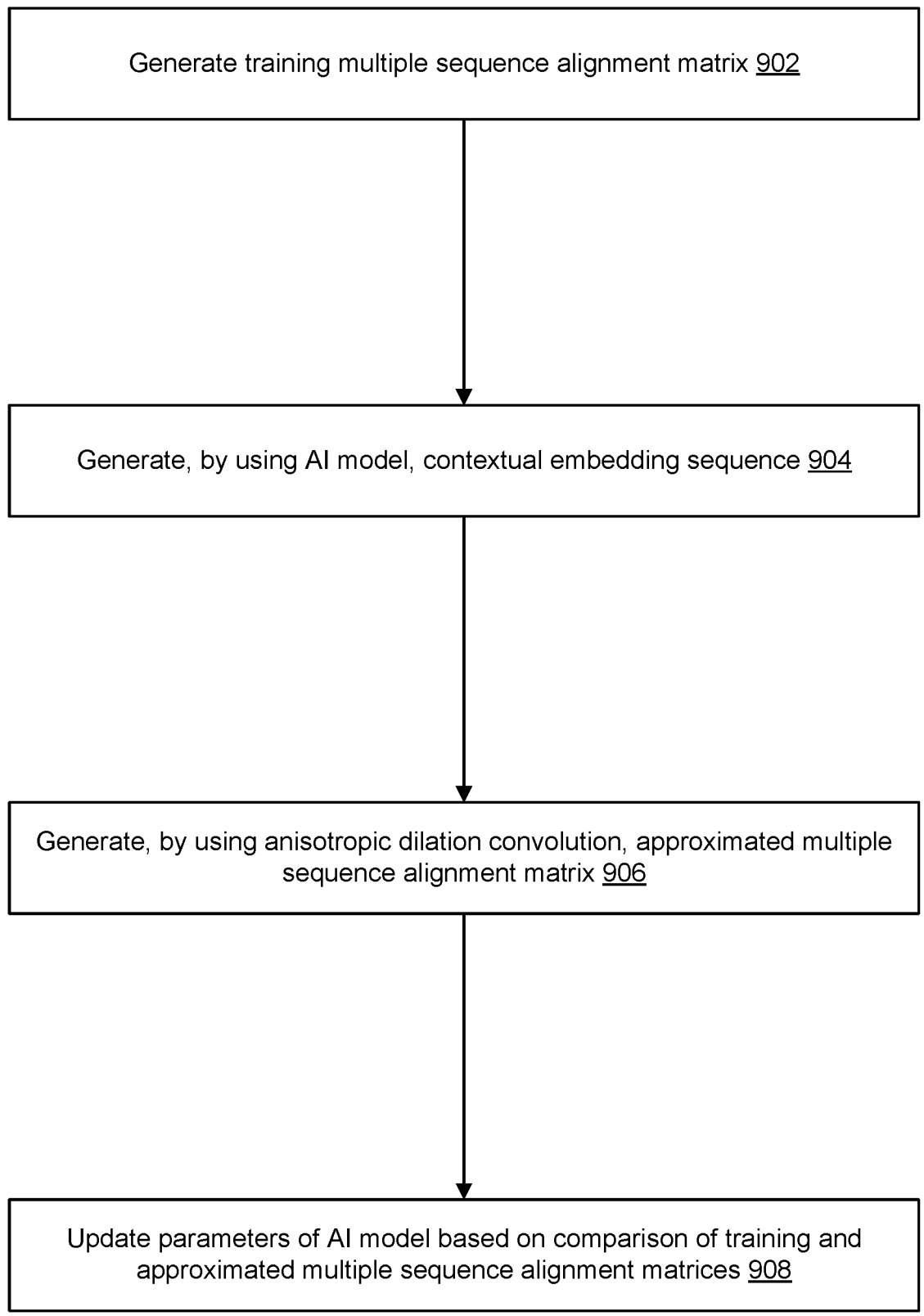
FIG. 9 illustrates an example of a flow for training an AI model to generate a contextual embedding sequence based on a MSA matrix according to embodiments of the present disclosure.

FIG. 9 illustrates an example of a flow for training an AI model to generate a contextual embedding sequence based on an MSA matrix according to embodiments of the present disclosure. A computer system, which may but need not be similar to the computer system of FIG. 1, is described as performing operations of the example flow of FIG. 9. Instructions for performing the operations can be stored as computer-readable instructions on one or more non-transitory computer-readable media of the computer system. As stored, the instructions represent programmable modules that include code or data executable by one or more processors of the computer system. The execution of such instructions configures the computer system to perform the specific operations shown in the corresponding figure and described herein. Each programmable module, in combination with the respective processor(s), represents a means for performing a respective operation(s). While the operations are illustrated in a particular order, it should be understood that no particular order is necessary and that one or more operations may be omitted, skipped, and/or reordered. Further, and as described herein above, a sequence of amino sequence is described. However, the flow similarly applies to a sequence of nucleotides or other compounds.

In an example, the flow can start operation 902, where the computer system generates an MSA matrix. Of course, another arrangement of protein sequences or biological sequences can be similarly generated and used in the training instead. In an example, multiple protein sequences are available from a data store. The computer system can randomly select one of them and use a BLAST process to identify related protein sequences and align them with the selected protein sequence in the training MSA matrix.

At operation 904, the computer system generates, by using an AI model, contextual embedding sequence. The AI model can be a contextual embedding AI model that is being trained. The training MSA matrix is input to the contextual embedding AI model that, in turn, outputs the contextual embedding sequence.

At operation 906, the computer system generates, by using an anisotropic dilation convolution, an approximated MSA matrix based on the contextual embedding sequence. For example, the anisotropic dilation convolution is performed on the embedding sequence to dilate it in order to have the same size as the training MSA matrix and approximate, through convolution, the training MSA matrix.

At operation 908 the computer system updates parameters of the AI model based on a comparison of the training MSA matrix and the approximated MSA matrix. For example, the comparison includes comparing differences between two matrices. An error function is expressed as a function of the differences. Backpropagation is used to update the parameters of the multi-dimensional convolutional layer of the AI model in order to reduce or minimize the error function. This process can be iterative across many training MSA matrices.

Figure 10:
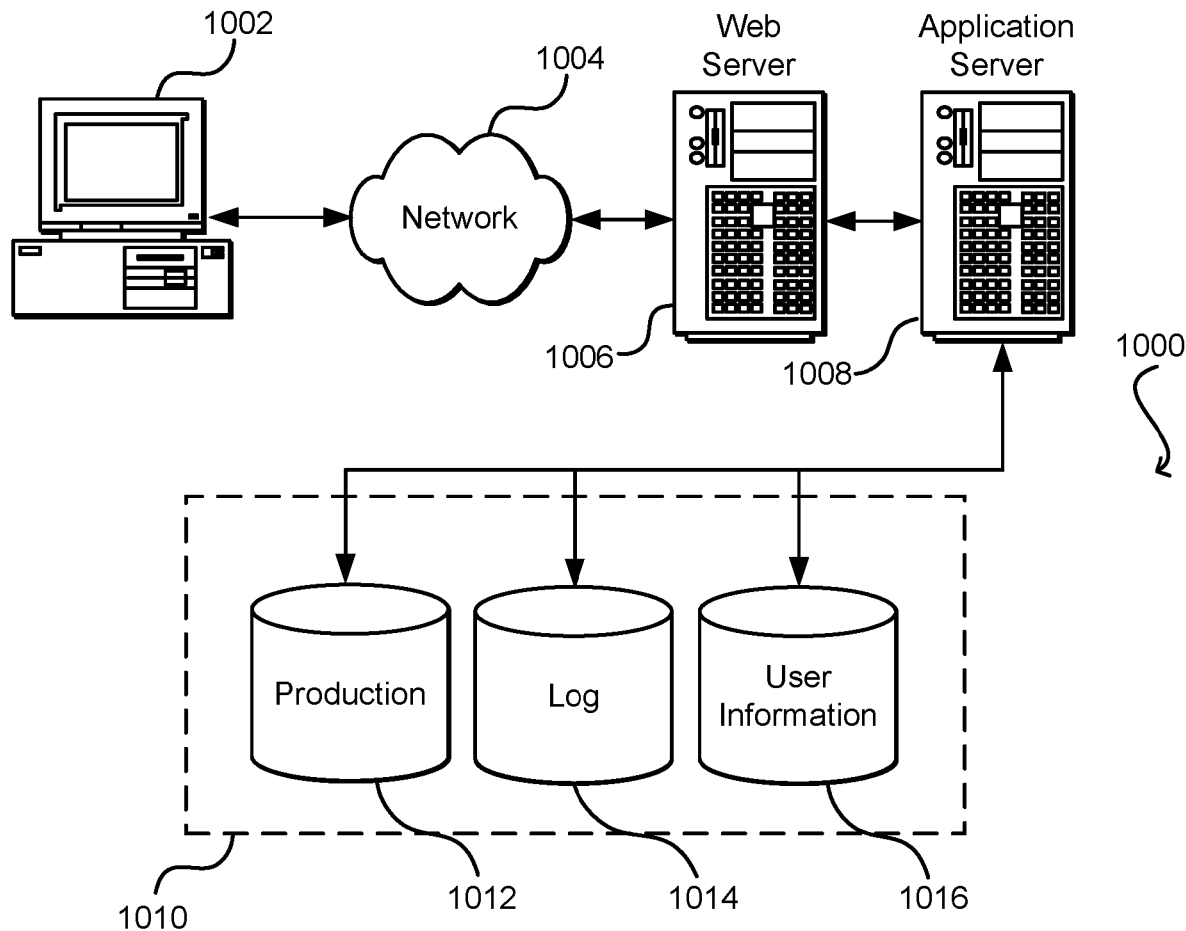
FIG. 10 illustrates aspects of an example environment for implementing aspects in accordance with various embodiments.

FIG. 10 illustrates a computer architecture diagram showing an example computer architecture, according to an embodiment of the present disclosure. This architecture may be used to implement some or all of the components of the computer systems (e.g., the computer system 100 of FIG. 1) described herein above. The computer architecture shown in FIG. 10 illustrates a server computer, workstation, desktop computer, laptop, tablet, network appliance, personal digital assistant ("PDA"), e-reader, digital cellular phone, or other computing device, and may be utilized to execute any aspects of the software components presented herein.

The computer 1000 includes a baseboard 1002, or "motherboard," which is a printed circuit board to which a multitude of components or devices may be connected by way of a system bus or other electrical communication paths. In one illustrative embodiment, one or more central processing units ("CPUs") 1004 operate in conjunction with a chipset 1006. The CPUs 1004 may be standard programmable processors that perform arithmetic and logical operations necessary for the operation of the computer 1000.

The CPUs 1004 perform operations by transitioning from one discrete, physical state to the next through the manipulation of switching elements that differentiate between and change these states. Switching elements may generally include electronic circuits that maintain one of two binary states, such as flip-flops, and electronic circuits that provide an output state based on the logical combination of the states of one or more other switching elements, such as logic gates. These basic switching elements may be combined to create more complex logic circuits, including registers, adders-subtractors, arithmetic logic units, floating-point units, and the like.

The chipset 1006 provides an interface between the CPUs 1004 and the remainder of the components and devices on the baseboard 1002. The chipset 1006 may provide an interface to a random access memory ("RAM") 1008, used as the main memory in the computer 1000. The chipset 1006 may further provide an interface to a computer-readable storage medium such as a read-only memory ("ROM") 1010 or non-volatile RAM ("NVRAM") for storing basic routines that help to startup the computer 1000 and to transfer information between the various components and devices. The ROM 1010 or NVRAM may also store other software components necessary for the operation of the computer 1000 in accordance with the embodiments described herein.

The computer 1000 may operate in a networked environment using logical connections to remote computing devices and computer systems through a network, such as the local area network 1020. The chipset 1006 may include functionality for providing network connectivity through a NIC 1012, such as a gigabit Ethernet adapter. The NIC 1012 is capable of connecting the computer 1000 to other computing devices over the network 1020. It should be appreciated that multiple NICs 1012 may be present in the computer 1000, connecting the computer to other types of networks and remote computer systems.

The computer 1000 may be connected to a mass storage device 1018 that provides non-volatile storage for the computer. The mass storage device 1018 may store system programs, application programs, other program modules, and data, which have been described in greater detail herein. The mass storage device 1018 may be connected to the computer 1000 through a storage controller 1014 connected to the chipset 1006. The mass storage device 1018 may consist of one or more physical storage units. The storage controller 1014 may interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 1000 may store data on the mass storage device 1018 by transforming the physical state of the physical storage units to reflect the information being stored. The specific transformation of physical state may depend on various factors, in different implementations of this description. Examples of such factors may include, but are not limited to, the technology used to implement the physical storage units, whether the mass storage device 1018 is characterized as primary or secondary storage, and the like.

For example, the computer 1000 may store information to the mass storage device 1018 by issuing instructions through the storage controller 1014 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 1000 may further read information from the mass storage device 1018 by detecting the physical states or characteristics of one or more particular locations within the physical storage units.

In addition to the mass storage device 1018 described above, the computer 1000 may have access to other computer-readable storage media to store and retrieve information, such as program modules, data structures, or other data. It should be appreciated by those skilled in the art that computer-readable storage media can be any available media that provides for the storage of non-transitory data and that may be accessed by the computer 1000.

By way of example, and not limitation, computer-readable storage media may include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

The mass storage device 1018 may store an operating system 1030 utilized to control the operation of the computer 1000. According to one embodiment, the operating system comprises the LINUX operating system. According to another embodiment, the operating system comprises the WINDOWS® SERVER operating system from MICROSOFT Corporation. According to further embodiments, the operating system may comprise the UNIX or SOLARIS operating systems. It should be appreciated that other operating systems may also be utilized. The mass storage device 1018 may store other system or application programs and data utilized by the computer 1000. The mass storage device 1018 might also store other programs and data not specifically identified herein.

In one embodiment, the mass storage device 1018 or other computer-readable storage media is encoded with computer-executable instructions which, when loaded into the computer 1000, transforms the computer from a general-purpose computing system into a special-purpose computer capable of implementing the embodiments described herein. These computer-executable instructions transform the computer 1000 by specifying how the CPUs 1004 transition between states, as described above. According to one embodiment, the computer 1000 has access to computer-readable storage media storing computer-executable instructions which, when executed by the computer 1000, perform the various routines described above. The computer 1000 might also include computer-readable storage media for performing any of the other computer-implemented operations described herein.

The computer 1000 may also include one or more input/output controllers 1016 for receiving and processing input from a number of input devices, such as a keyboard, a mouse, a touchpad, a touch screen, an electronic stylus, or other type of input device. Similarly, the input/output controller 1016 may provide output to a display, such as a computer monitor, a flat-panel display, a digital projector, a printer, a plotter, or other type of output device. It will be appreciated that the computer 1000 may not include all of the components shown in FIG. 10, may include other components that are not explicitly shown in FIG. 10, or may utilize an architecture completely different than that shown in FIG. 10. It should also be appreciated that many computers, such as the computer 1000, might be utilized in combination to embody aspects of the various technologies disclosed herein.

The specification and drawings are, accordingly, to be regarded in an illustrative rather than a restrictive sense. It will, however, be evident that various modifications and changes may be made thereunto without departing from the broader spirit and scope of the disclosure as set forth in the claims.

Other variations are within the spirit of the present disclosure. Thus, while the disclosed techniques are susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions and equivalents falling within the spirit and scope of the invention, as defined in the appended claims.

The use of the terms "a" and "an" and "the" and similar referents in the context of describing the disclosed embodiments (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this disclosure are described herein, including the best mode known to the inventors for carrying out the invention. Variations of those preferred embodiments may become apparent to those of ordinary skill in the art upon reading the foregoing description. The inventors expect skilled artisans to employ such variations as appropriate and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications and patents, cited herein are hereby incorporated by reference to the same extent as if each reference were individually and specifically indicated to be incorporated by reference and were set forth in its entirety herein.

What is claimed is:

1. A system, comprising:
    one or more processors; and
    one or more memories storing computer-readable instructions that, upon execution by the one or more processors, configure the system to:
        receive first data indicating a first biological sequence of a subject, the first data determined based at least in part on tumor cells of the subject;
        determine, based at least in part on a look up to a data store storing biological sequences, second data indicating a sequence arrangement that comprises a second biological sequence and a component of the first biological sequence;
        generate, by at least using a convolutional layer of a machine learning (ML) model, multi-dimensional data that represents an embedding associated with the sequence arrangement, the convolutional layer generating the multi-dimensional data based at least in part on the second data and on an iterative encoding loop between the convolutional layer and an anisotropic pooling layer of the ML model, the iterative encoding loop increasing an embedding dimension of the multi-dimensional data;
        generate, by at least using at least using the anisotropic pooling layer, a contextual embedding vector corresponding to the component of the first biological sequence, the anisotropic pooling layer generating the contextual embedding vectors based at least in part on the multi-dimensional data and the iterative encoding loop; and
        cause a vaccine to be produced based at least in part on the contextual embedding vector, the vaccine associated with the first biological sequence and targeting a tumor exhibited by the tumor cells.

2. The system of claim 1, wherein the component is an amino acid and the sequence arrangement is a multiple sequence alignment (MSA) matrix, and wherein the one or more memories store further computer-readable instructions that, upon execution by the one or more processors, additionally configure the system to:
    generate, as part of the iterative encoding loop, a first image having a length "L" corresponding to a total number of the amino acids in the first biological sequence, a height "H" corresponding to a total number of rows in the MSA matrix, and a first embedding dimension "$D_{in}$";
    input the first image to the convolutional layer, wherein the convolutional layer outputs a second image having the length "L", the height "H", and a second embedding dimension "$D_{out}$" that is larger than the first embedding dimension "$D_{in}$"; and
    input the second image to the anisotropic pooling layer, wherein the anisotropic pooling layer outputs the contextual embedding vector by at least reducing, per embedding dimension, the height "H" and preserving the length "L" of the second image.

3. The system of claim 1, wherein the component is an amino acid and the sequence arrangement is a multiple sequence alignment (MSA) matrix, and wherein the one or more memories store further computer-readable instructions that, upon execution by the one or more processors, additionally configure the system to train the ML model by at least:
    generating a first training MSA matrix from a plurality of protein sequences stored in the data store;
    generating first training data by at least inputting the training MSA matrix to the ML model, wherein the first training data comprises embedding vectors;
    generating a second training MSA matrix by at least performing an anisotropic dilated convolution on the first training data; and
    updating parameters of the ML model based on a comparison of the first training MSA matrix and the second training MSA sequence.

4. A method implemented on a system, the method comprising:
    receiving first data indicating a first biological sequence;
    determining second data indicating a sequence arrangement that comprises a second biological sequence and a component of the first biological sequence;
    generating, by at least using a convolutional layer of a machine learning (ML) model, multi-dimensional data that represents an embedding associated with the sequence arrangement, the convolutional layer generating the multi-dimensional data based at least in part on the second data and on an iterative encoding loop between the convolutional layer and an anisotropic pooling layer of the ML model, the iterative encoding loop increasing an embedding dimension of the multi-dimensional data;

generating, by at least using at least using the anisotropic pooling layer, a contextual embedding vector corresponding to the component of the first biological sequence, the anisotropic pooling layer generating the contextual embedding vectors based at least in part on the multi-dimensional data and the iterative encoding loop; and causing a vaccine to be produced based at least in part on the contextual embedding vector, the vaccine associated with the first biological sequence.

5. The method of claim 4, further comprising:
generating a biological sequence prediction by at least inputting the contextual embedding vector to another ML model that outputs the biological sequence prediction.

6. The method of claim 4, wherein the convolution layer and the anisotropic pooling layer perform a first convolution and a first anisotropic pooling, respectively, in a first iteration, and wherein the method further comprises:
performing, in a second iteration by the convolutional layer, a second convolution on an output of the first anisotropic pooling; and
perform, in a second iteration by the anisotropic pooling layer, a second anisotropic pooling on an output of the second convolution, wherein the first convolution and the second convolution preserve a length of a third sequence of contextual embedding vectors, and wherein the first anisotropic pooling and the second anisotropic pooling increasingly reduce a height of the third sequence.

7. The method of claim 4, wherein the anisotropic pooling layer performs a first anisotropic pooling in a first iteration, and wherein the method further comprises:
performing, in a second iteration by the anisotropic pooling layer, a second anisotropic pooling on an output of a second convolution, wherein a kernel size of the first anisotropic pooling is different from a kernel size of the second anisotropic pooling.

8. The method of claim 4, wherein the anisotropic pooling layer performs anisotropic max pooling in an iteration, wherein a kernel size of the anisotropic max pooling is based at least in part on the iteration and a total number of sequences included in the sequence arrangement.

9. The method of claim 4, wherein the anisotropic pooling layer performs anisotropic max pooling in an iteration, wherein a kernel size of the anisotropic max pooling is set to a value from a set of kernel sizes, wherein a product of the kernel sizes equals a total number of sequences included in the sequence arrangement.

10. The method of claim 4, wherein the anisotropic pooling layer performs anisotropic max pooling, wherein a kernel size of the anisotropic max pooling has a height and a length, wherein the height is larger than the length, and wherein a stride of the anisotropic max pooling equals to the kernel size.

11. The method of claim 4, wherein the sequence arrangement is a multiple sequence alignment (MSA) matrix, and wherein the method further comprises:
generating a first image having a length "L" corresponding to a total number of amino acids in the first biological sequence, a height "H" corresponding to a number of rows in the MSA matrix, and a first embedding dimension "$D_{in}$"; and
inputting the first image to the convolutional layer of the ML model, wherein the convolutional layer outputs a second image having the length "L", the height "H", and a second embedding dimension "$D_{out}$".

12. The method of claim 11, further comprising:
inputting, per embedding dimension, a corresponding set of "L×H" pixels of the second image to the anisotropic pooling layer.

13. The method of claim 11, further comprising:
inputting, during a first iteration of the iterative encoding loop, an output of the convolutional layer of the ML model to the anisotropic pooling layer, wherein, during the first iteration, the height "H" is reduced and the length "L" is preserved by the anisotropic pooling layer; and
inputting, during a second iteration of the iterative encoding loop, an output of the anisotropic pooling layer to the convolutional layer, wherein during the second iteration, the second embedding dimension "$D_{out}$" is increased by the convolutional layer.

14. One or more non-transitory computer-readable storage media storing instructions that, upon execution on a system, cause the system to perform operations comprising:
receiving first data indicating a first biological sequence;
determining second data indicating a sequence arrangement that comprises a second biological sequence and a component of the first biological sequence;
generating, by at least using a convolutional layer of a machine learning (ML) model, multi-dimensional data that represents an embedding associated with the sequence arrangement, the convolutional layer generating the multi-dimensional data based at least in part on the second data and on an iterative encoding loop between the convolutional layer and an anisotropic pooling layer of the ML model, the iterative encoding loop increasing an embedding dimension of the multi-dimensional data;
generating, by at least using at least using the anisotropic pooling layer, a contextual embedding vector corresponding to the component of the first biological sequence, the anisotropic pooling layer generating the contextual embedding vectors based at least in part on the multi-dimensional data and the iterative encoding loop; and
causing a vaccine to be produced based at least in part on the contextual embedding vector, the vaccine associated with the first biological sequence.

15. The one or more non-transitory computer-readable storage media of claim 14 storing further instructions that, upon execution on the system, cause the system to perform additional operations comprising:
generating a first image having a length "L" corresponding to a total number of components in the first biological sequence, a height "H" corresponding to a number of rows in the sequence arrangement, and a first embedding dimension "$D_{in}$"; and
iteratively performing convolution and anisotropic pooling, wherein the first image is used in an initial iteration of the iterative encoding loop, and wherein a third sequence is an output after a last iteration, comprises the contextual embedding vector, and has the length "L", a height of one, and an embedding dimension "$D_{out}$".

16. The one or more non-transitory computer-readable storage media of claim 14 storing further instructions that, upon execution on the system, cause the system to perform additional operations comprising:
including the first biological sequence in a top row of a multiple sequence alignment (MSA) matrix, wherein the sequence arrangement is the MSA matrix, and wherein anisotropic pooling is performed by the anisotropic pooling layer by at least applying a kernel starting at a position that corresponds to a location in the top row.

17. The one or more non-transitory computer-readable storage media of claim 14 storing further instructions that, upon execution on the system, cause the system to perform additional operations comprising:
including the first biological sequence in a first row of a multiple sequence alignment (MSA) matrix, wherein the sequence arrangement is the MSA matrix, and wherein the MSA matrix and the first biological sequence have a same length;
and including the second biological sequence in a second row of the MSA matrix, wherein the second biological sequence is padded to have the same length.

18. The one or more non-transitory computer-readable storage media of claim 14 storing further instructions that, upon execution on the system, cause the system to perform additional operations comprising:
shuffling biological sequences included in a multiple sequence alignment (MSA) matrix prior to inputting the MSA matrix to the ML model, wherein the sequence arrangement is the MSA matrix.

19. The one or more non-transitory computer-readable storage media of claim 14 storing further instructions that, upon execution on the system, cause the system to perform additional operations comprising:
determining that a total number of available biological sequences is smaller than a target height of a multiple sequence alignment (MSA) matrix, wherein the sequence arrangement is the MSA matrix; and
including the second biological sequence in a first row and a second row of the MSA matrix.

20. The one or more non-transitory computer-readable storage media of claim 14 storing further instructions that, upon execution on the system, cause the system to perform additional operations comprising:
determining that a total number of available biological sequences is larger than a target height of a multiple sequence alignment (MSA) matrix, wherein the sequence arrangement is the MSA matrix; and
removing a third biological sequence from the MSA matrix.

* * * * *